United States Patent [19]

Hasson

[11] Patent Number: 5,368,598
[45] Date of Patent: Nov. 29, 1994

[54] METHOD OF MANIPULATING AN UTERUS USING A BENDABLE MANIPULATOR

[76] Inventor: Harrith M. Hasson, 2043 N. Sedgwick, Chicago, Ill. 60614

[21] Appl. No.: 72,729

[22] Filed: Jun. 7, 1993

Related U.S. Application Data

[63] Continuation-in-part of Ser. No. 688,114, Apr. 19, 1991, Pat. No. 5,217,466, and a continuation-in-part of Ser. No. 62,923, May 13, 1993.

[51] Int. Cl.⁵ .............................................. A61B 17/42
[52] U.S. Cl. .................................. 606/119; 606/191; 128/20; 128/898
[58] Field of Search ................. 128/20, 898; 606/119, 606/121-125, 190, 191, 192, 193, 198, 1; 604/164, 264

[56] References Cited

U.S. PATENT DOCUMENTS

| | | |
|---|---|---|
| 735,400 | 8/1903 | McCully . |
| 923,303 | 6/1909 | Shults .................................. 606/193 |
| 2,905,178 | 9/1959 | Hilzinger, III . |
| 3,796,211 | 3/1974 | Kohl . |
| 3,805,767 | 4/1974 | Erb . |
| 3,809,091 | 5/1974 | Shute ................................... 606/119 |
| 3,877,433 | 4/1975 | Librach . |
| 4,000,743 | 1/1977 | Weaver . |
| 4,022,208 | 5/1977 | Valtchev . |
| 4,781,704 | 11/1988 | Potter . |
| 4,935,017 | 6/1990 | Sylvanowicz . |
| 4,960,411 | 10/1990 | Buchbinder . |
| 4,969,875 | 11/1990 | Ichikawa . |
| 4,976,717 | 12/1990 | Boyle ................................... 606/119 |
| 4,986,814 | 1/1991 | Burney et al. . |
| 4,997,419 | 3/1991 | Laktos et al. . |
| 5,020,195 | 6/1991 | LeVahn ................................ 128/20 |
| 5,026,350 | 6/1991 | Tanaka et al. . |

Primary Examiner—Stephen C. Pellegrino
Assistant Examiner—Glenn K. Dawson
Attorney, Agent, or Firm—Wood, Phillips, VanSanten, Hoffman & Ertel

[57] ABSTRACT

A method of repositioning at least one of an organ and a vessel by performing the steps of: providing an instrument having an elongate section with an exposed surface; directing the elongate section into one of an organ and a vessel with the elongate section in a first state; and reconfiguring the elongate section to a second state to thereby cause the exposed surface of the elongate section to bear against the one of the organ and vessel to thereby effect positioning of the one of the organ and vessel.

9 Claims, 4 Drawing Sheets

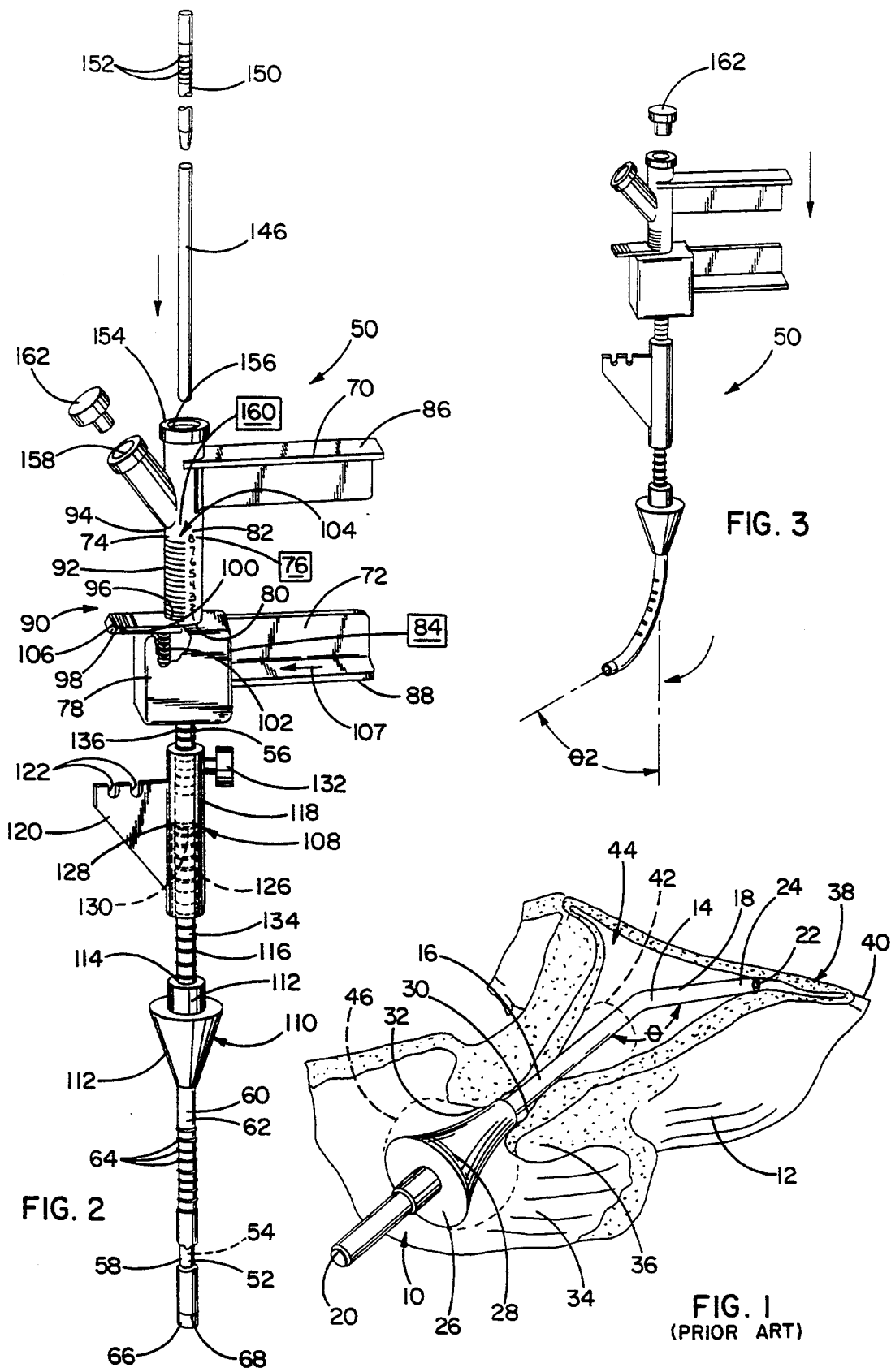

METHOD OF MANIPULATING AN UTERUS USING A BENDABLE MANIPULATOR

CROSS-REFERENCE

This application is a continuation-in-part of Ser. No. 688, 114, filed Apr. 19, 1991 and entitled "Guide for Facilitating the Performance of Internal Surgery", now U.S. Pat. No. 5,217,466, and Ser. No. 08/062,923, filed May 13, 1993 and entitled "Support for Surgical Instrument", pending.

BACKGROUND OF THE INVENTION

1. Field of the Invention

This invention relates to surgical instruments and, more particularly, to a method of controllably repositioning organs and vessels within a body cavity to facilitate the performance of surgical procedures.

2. Background Art

It is common to perform a number of medical procedures on female patients without making an incision by using endoscopic techniques, to include a) laparoscopy to perform surgery on pelvic organs by passing a telescope (laparoscope) through a small abdominal incision (an artificial opening) to gain access to the pelvis and b) hysteroscopy to perform intrauterine surgery by introducing a telescope (hysteroscope) through the natural vaginal and cervical openings to access the uterus. In the case of laparoscopy, the surgeon needs to use a dependable uterine manipulator to reposition the uterus to permit access to the region at which a procedure is to be performed. In the case of hysteroscopy, stabilizing and maintaining the position of the telescope within the uterus permits the surgeon to perform intrauterine procedures without fatigue and with precision.

The need for uterine manipulation is most pronounced where the uterus assumes a retroverted position, which is common for woman who have borne children. The surgeon is required to place the retroverted uterus into an anterior position to carry out most intrauterine procedures.

Uterine manipulation may be effected during a procedure by the surgeon or by an assistant. It is difficult and counterproductive for the surgeon to both reposition the uterus with an instrument in one hand and perform the procedure through a separate instrument held by the other hand.

Further, because the uterus is flexible and tends naturally towards one orientation, i.e. the retroverted position, the surgeon must constantly maintain a repositioning force on the uterus throughout a procedure. Not only is this activity tiring, but it is very difficult for the surgeon to maintain a consistent orientation of the uterus, particularly when the surgeon is simultaneously carrying out what is normally a delicate medical procedure.

If the uterine manipulation is carried out by an assistant, other problems are created. The assistant takes up valuable space in an operating room and by being positioned in front of the surgeon between the legs of the patient may interfere with the surgeon's view of a monitor through which the surgeon is able to observe the procedure.

It is equally difficult and wasteful for an assistant to be dedicated to the tasks of positioning, and maintaining the desired position of, the uterus throughout a surgical procedure. This is because certain uterine positions are difficult to maintain with manual pressure and because conventional manipulators do not lend themselves to automatically holding a uterine position, thereby requiring constant manual pressure, which is awkward and causes fatigue.

A multitude of different instruments have been devised to reposition the uterus. In each of U.S. Pat. No. 3,877,433, to Librach, U.S. Pat. No. 4,000,743, to Weaver, and U.S. Pat. No. 4,022,208, to Valtchev, instruments are disclosed wherein the distal end of the instrument is repositionable by being pivoted as a unit relative to a main body. Each of these instruments requires a relatively complicated linkage that permits this repositioning. This linkage may add considerably to the cost of an instrument, reduce its reliability, and make it undesirably cumbersome.

A further problem with these prior art instruments is that they may be relatively difficult to operate in use. As can be seen in FIGS. 1 and 2 of Weaver, a substantial lengthwise force must be exerted on the operating wire to effect the pivoting of the distal end of the instrument. There is a relatively small moment arm for the pivoting which requires that a large force be exerted on the wire. It is thus prone to breakage.

It is very important that the surgeon be able to maintain a desired position for a uterus. In the event that the desired position of a uterus is not maintained, tension on the tissues is affected and access to the region at which a procedure is to be performed is impaired, complicating and undesirably lengthening the time necessary for the procedure. The surgeon risks damaging adjacent tissues and organs because of lack of proper visualization and absence of tension on the affected tissue planes.

SUMMARY OF THE INVENTION

The present invention is specifically directed to overcoming the above enumerated problems in a novel and simple manner.

The present invention contemplates a method of repositioning at least one of an organ and a vessel by performing the steps of: providing an instrument having an elongate section with an exposed surface; directing the elongate section into one of an organ and a vessel with the elongate section in a first state; and reconfiguring the elongate section to a second state to cause the exposed surface of the elongate section to bear against the one of the organ and vessel to thereby effect positioning of the one of the organ and vessel.

The elongate section preferably can be fixed in its second state to thereby firmly and consistently maintain the one of the organ and vessel in a desired position.

In a preferred form, the elongate section includes first and second tubes, at least partially one within the other, connected to each other so that lengthwise movement of one of the tubes relative to the other causes the other tube to bend to thereby reconfigure the elongate section.

With this arrangement, the elongate section can be made very compact, without the need of complicated linkages. At the same time, the one of the organ and vessel can be positively controllably manipulated.

A ratchet or similar type of mechanism can be employed to maintain the elongate section in a plurality of predetermined states between the first and second states.

Visual identification structure can be provided to give the surgeon an awareness of the configuration of the elongate section and thus the position of the organ/vessel being repositioned thereby from externally of the patient.

The instrument can be attached to the patient or a separate support. In the former case, structure can be provided to block instrument insertion at a predetermined position. In the latter case, consistent orientation of the instrument can be maintained without relying on flexible portions of the patient which are normally resilient and prone to repositioning.

For ease of operation, the elongate section is reconfigured by controlling first and second arms. At least one of the first and second arms is movable relative to the other, and preferably this relative movement is in translation. The surgeon can conveniently grasp the handles and squeeze them to effect the reconfiguration of the elongate section. By making the arms long enough, one arm can be placed in the palm of the surgeon's hand with a plurality of fingers being available to positive squeeze the arms towards each other.

The elongate section can be made hollow to accommodate a separate instrument which can be controllably passed therethrough.

The inventive method can be used in a wide range of surgical procedures, but is particularly desirable in repositioning a uterus, as from a retroverted position to an anterior position. In this procedure, the instrument can be readily attached to the cervix, as through the use of a tenaculum.

BRIEF DESCRIPTION OF THE DRAWINGS

FIG. 1 is a perspective view of a prior art surgical guide structure operatively associated with a uterus;

FIG. 2 is a perspective view of a preferred form of surgical guide structure according to the present invention and showing a guide tube thereon in a straight orientation;

FIG. 3 is a view as in FIG. 2 with the guide tube set at a predetermined bend angle;

DETAILED DESCRIPTION OF THE DRAWINGS

Figure 4:
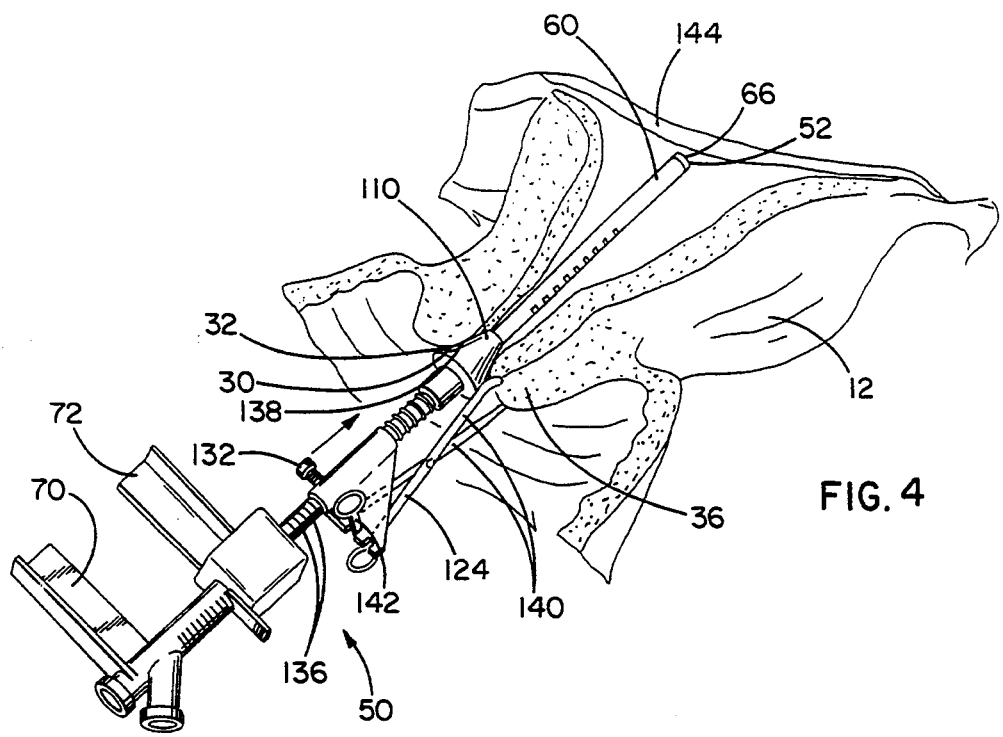
FIG. 4 is a perspective view of the inventive guide structure placed operatively within a uterus in its FIG. 2 orientation.

In FIG. 1, a prior art guide structure for facilitating the performance of intrauterine surgery is shown at 10 in operative association with a uterus 12. The guide structure 10 consists of a metal guide tube 14 having a straight body 16 and an offset end 18 making an angle $\Theta$ with the body 16. The guide tube 14 defines an internal passageway 20 for guiding a surgical instrument from a point externally of the uterus 12, through the uterus 12, and angularly outwardly through an opening 22 at the distal end 24 of the guide tube 14.

The guide tube 14 has a surrounding sealing member 26 which is movable lengthwise relative to the guide tube body 16. The sealing member 26 has a tapered sealing surface 28 which is directed into the cervical canal 30 to seal the cervical opening 32.

To place the guide structure 10 in its operative position, the offset guide tube end 18 must be forced through the cervical canal 30. This requires that the surgeon tilt the entire guide structure 10. Even by tilting the guide structure 10 to the maximum extent permitted within the vagina 34, the cervix 36 must be stretched. This may cause pain and/or injury to the patient. Once the offset end 18 is directed through the cervical canal 30, the offset end 18 may hang up on the uterus 12 as it is directed into its operative position of FIG. 1, in which the length of the offset end 18 is aligned at the uterotubal junction 38 to facilitate direction of an instrument into the fallopian tube 40.

Once the guide tube 14 is in its operative position, a bladder 42 can be inflated to maintain the sealing member 26 securely in the cervical opening 32 and thereby seal the uterine cavity 44. The bladder 42 may cause discomfort to the patient and may possibly induce spasms that hamper the performance of the surgical procedure.

In FIG. 1, an optional bladder 46 is shown externally of the uterine cavity 44 to cooperate with the bladder 42 to maintain the guide structure 10 in place and the uterine cavity 44 sealed. The bladder 46 may be used as an alternative to the more rigid sealing member 26 in FIG. 1.

In FIGS. 2–5, a first form of a guide structure for surgical instruments, according to the present invention, is shown at 50. The guide structure 50 consists of a flexible guide tube 52, made preferably from plastic and defining an internal working passageway 54. The guide tube 52 has proximal and distal ends 56, 58, respectively, with the distal end 58 being advanceable through an opening in tissue surrounding a cavity in which a surgical procedure is to be performed.

The guide tube 52 is surrounded by a second flexible/plastic tube 60 having a peripheral wall 62 with a plurality of axially spaced slits 64 therethrough. The free end 66 of the guide tube 52 is connected to the free end 68 of the second tube 60. By attempting to draw the second tube 60 upwardly/axially relative to the guide tube 52, the second tube is caused to collapse/bend, as readily permitted by the slits 64, as shown in FIG. 3. The bend angle for the distal end 58 of the guide tube 52 is identified as $\Theta 2$ in FIG. 3 and preferably ranges from 0°–90°.

Relative lengthwise shifting between the guide tube 52 and second tube 60 is accomplished through first and second arms 70, 72, respectively. The first arm 70 projects radially from a cylindrical sleeve 74 at the proximal end of the guide structure 50. The arm 70 has an L-shaped cross section to give it rigidity. The sleeve 74 is fixedly secured to the guide tube 52 by a means shown schematically at 76. The construction of a suitable securing means 76 is within the knowledge of one skilled in the art.

A squared housing 78 has a guide opening 80 therethrough and supports the second arm 72 in cantilever fashion. The body 82 of the sleeve 74 is movable within the opening 80 to permit guided movement of the arms 70, 72 towards and away from each other. The housing 78 is fixedly secured by a means 84, also of a type well known to those skilled in the art, to the second tube 60. The second arm 72 has an L-shaped cross section as the first arm 70. The arms 70, 72 are arranged so that oppositely facing flat surfaces 86, 88 on the arms 70, 72, respectively, can be readily grasped by the user who can then squeeze the arms 70, 72 in one hand to effect movement of the arms 70, 72, one towards the other. As this occurs, the guide and second tubes 52, 60 shift and resultingly the distal end 58 of the guide tube 52 is progressively bent.

To facilitate setting and holding of the desired bend angle Θ2 for the distal end 58 of the guide 52, a ratchet mechanism is provided at 90. The ratchet mechanism 90 consists of a plurality of axially spaced teeth 92 on the outer surface 94 of the sleeve 74. The teeth 92 cooperate with a curved edge 96 on a ratchet tab 98 that is pivotable about a pin 100 to selectively a) place the edge 96 in engagement with the teeth 92 and b) separate the edge 96 from the teeth 92.

The tab 98 is normally biased by a spring 102 to a neutral position in which the edge 96 resides between adjacent teeth 92. As the sleeve 74 moves downwardly into the guide opening 80, the edge 96 moves in and out between adjacent teeth 92 against the bias of the spring 102. The cooperating tab 98 and teeth 92 thus maintain the guide and second tubes 52, 60 in a desired relationship to produce and maintain a range of bend angles for the distal end 58 of the guide tube 52. The teeth 92 serve as graduations which are numbered as at 104 to give a visual indication of the relative positions of the guide and second tubes 52, 60 and allow consistent re-setting of the bend angle for the guide tube 52.

By pressing down on a ribbed surface 106 of the tab 98, the tab 98 pivots about the pin 100 to disengage the edge 96 from the teeth 92 to allow unimpeded relative movement between the guide and second tubes 52, 60.

Preferably, the arms 70, 72 have their lengths generally aligned to be parallel with the path traced by the distal end 58 of the guide tube 52 as it is repositioned. Consequently, the operator of the guide structure 50 can readily visually determine the direction of bending and amount of bend angle for the guide tube 52 from outside of the cavity in which the surgery is performed. An indicating arrow 107 (FIG. 1) on the arm 72 gives a further visual indication of the bending direction of the guide tube 52.

To facilitate mounting of the guide tube 52 with respect to a tissue through which the guide structure is extended, an outer sleeve 108 and sealing member 110 are provided on the second tube 60 and are each slidable lengthwise therealong. The sealing member 110 has a conical surface 112 which seals an opening through which the guide structure 50 extends, as described below. The sealing member 110 has a cylindrical extension 112 defining a receptive socket 114 for one end of a spring 116 that is utilized to bias the sealing member 110 away from the outer sleeve 108.

The outer sleeve 108 has a cylindrical body 118 with a radially projecting arm 120 which facilitates securing of the guide structure 50 with respect to tissue through which the guide structure 50 extends. The arm 120 has radially spaced notches 122 for mounting a tenaculum 124 (FIG. 4), as described in detail below. The body 118 has a stepped bore 126 therethrough defining a shoulder 128 for the spring end 130. A locking screw 132 fixes the body 118 in desired position along the second tube 60.

The outer surface 134 of the second tube 60 has graduations 136 thereon to give the user a visual indication of the relative positions of the guide and second tubes 50, 60, respectively. This alerts the user to the amount of extension of the distal tube end 58 into a cavity.

The application of the guide structure 50 will now be described with respect to FIGS. 4 and 5, which show the guide structure 50 operatively associated with a uterus 12. With the guide tube 52 in its straight position of FIG. 2, it can be conveniently directed through the cervical canal 30 with minimal resistance. The sealing member 110 is then pressed into the cervical opening 32 in sealing engagement with the surrounding cervical wall 138. The working end of the tenaculum 124, which is of a conventional construction, has jaws 140 which cooperatively grip the cervix 36. The opposite end of the tenaculum 124 has a holding bar 142 which is then placed in one of the notches 122 on the securing arm 120 on the outer sleeve 108. This results in the sleeve 108 being held in a substantially fixed position relative to the cervix 36 and causes the spring 116 to thereby exert an inward bias on the sealing member 110 which thereby effects a positive seal at the cervical opening 32. At the same time this arrangement straightens out any degree of ante- or retroversion which would occur in the absence of the tenaculum 124.

The guide and second tubes 52, 60 are then pressed into the uterus until the free end 66 of the guide tube 52 encounters the top of the fundus 144. The guide and second tubes 52, 60 are then backed out from 0.5 to 1.5 centimeters to optimize the position of the guide tube 52. This position for the guide and second tubes 52, 60 is then maintained by the locking screw 132.

To facilitate direction of the guide tube 52 into place without buckling, an optional stiffening rod 146 (FIG. 2) can initially be extended through the guide tube 52. Once the guide tube 52 is in place, the stiffening rod 146 can be removed to open the passageway 54 defined by the guide tube 52. The amount of extension of the guide tube 52 into the uterus 12 can be readily ascertained by observing the graduations 136 on the second tube 60.

Figure 5:
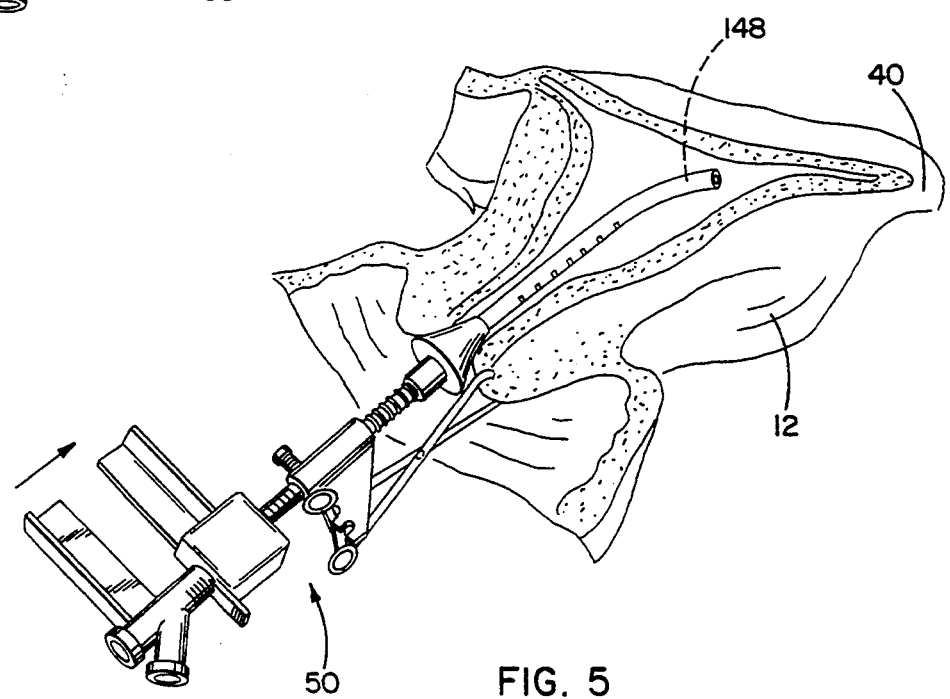
FIG. 5 is a view as in FIG. 4 with the guide tube bent to facilitate direction of an instrument into the fallopian tube.

The user can then urge the arms 70, 72 towards each other to produce the desired bend angle, as shown in FIG. 5. The ratchet mechanism 90 maintains the desired bend angle for the distal end 58 of the guide tube 52.

The teeth 92 are preferably spaced sufficiently close together that fine adjustments to the bend angle can be made. The preferred bend angle in FIG. 5 aligns the line of the bent portion 48 at the distal end 58 of the guide tube 52 with the fallopian tube 40 to facilitate passage of an instrument thereinto. The invention does contemplate various other structures for setting and maintaining the bend angle for the guide tube 52.

A measuring tube 150 can be directed through the guide structure 50 in its operative position of FIG. 5. The tube 150 has graduations 152 thereon to give the user a visual indication of the distance from the top edge 154 of the guide structure 50 to the free end 66 of the guide tube 52. By withdrawing the measuring tube 150, the user can then determine the exact length of instrument required to be directed through the guide structure 50 into the fallopian tube 40.

Once the procedure is completed, the tenaculum 124 can be released to allow withdrawal of the entire guide structure 50.

Another aspect of the invention is the provision of separate ports 156, 158 in communication with the tube passageway 54. The primary port 156 defines the entryway for the surgical instruments that are employed. The secondary port 158 provides means for injecting a fluid into a cavity, which fluid may be saline or a dye, depending upon the procedure. An optional one-way valve 160 can be used to allow introduction of instruments and fluid while obstructing return flow of fluid through the passageway 54. A sealing cap 162 can be removably placed in each of the ports 156, 158 to effect sealing thereof.

Figure 6:
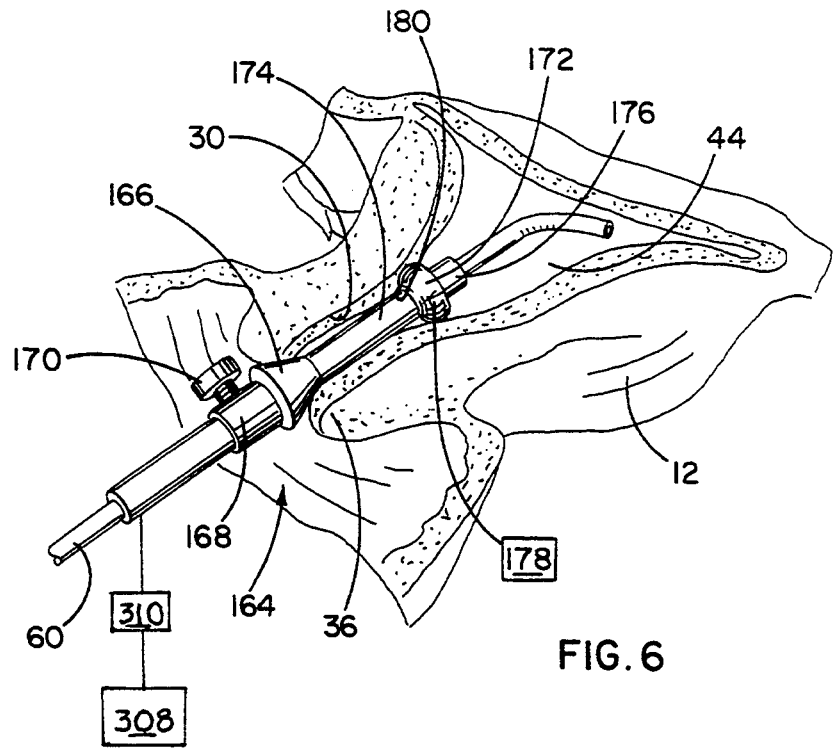
FIG. 6 is a modified form of guide structure for a surgical instrument according to the present invention, operatively positioned within a uterus, and, as shown in phantom lines, having a distal section which is movable to reposition a uterus.

If internal, optical monitoring of a procedure is carried out, a modified form of the guide structure according to the present invention, as shown at 164 in FIG. 6, can be employed. The guide structure 164 employs a conical sealing member 166 with a sleeve extension 168 and locking nut 170 thereon and a spaced, inflatable bladder 172, shown in FIG. 6 in its inflated state. The sealing member 166 and bladder 172 are incorporated into a guide tube 174 that is directed through the cervical canal 30. The bladder 172 is provided at the distal end 176 of the guide tube 174. The sealing member 166 and associated sleeve 168 are slidable towards and away from the bladder 172 on the guide tube 174.

Once the guide tube 174 is inserted through the cervical canal 30, the bladder 172 can be inflated through a supply 178 of liquid or gas to define a shoulder 180 that prevents withdrawal of the bladder from the uterine cavity 144. The sleeve extension 168 and sealing member 166 can then be slid towards the bladder 172 so that the cervix 36 is held captive between the bladder 172 and sealing member 166.

The second tube 60 and guide tube 52 can then be directed as a unit through the tube 174 into operative position as in the previously described embodiment.

If the procedure is monitored optically, it is unnecessary to provide the scale to determine the exact bend angle for the guide tube 52 as well as the amount of extension into the uterus 12. The surgeon can visually monitor the position and angle of the guide tube 42.

Figure 7:
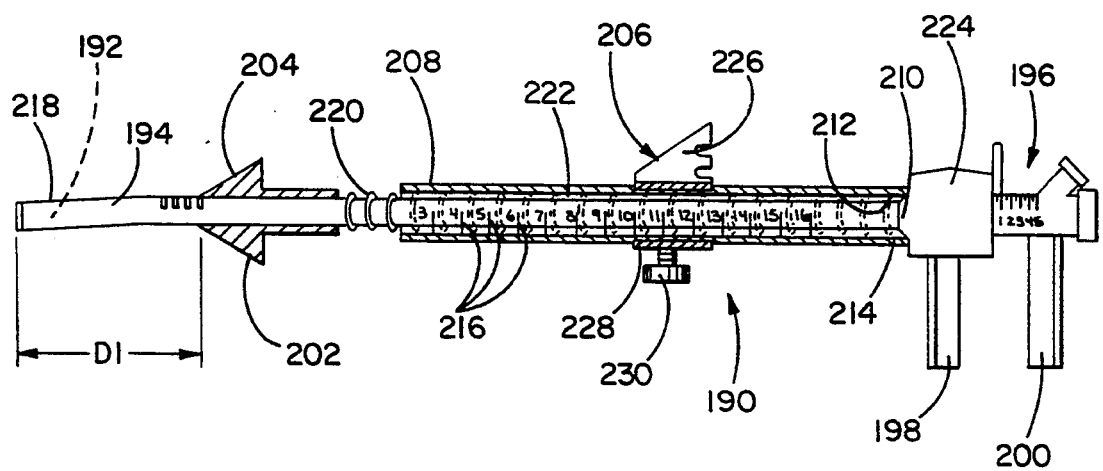
FIG. 7 is a side elevation view of a further modified form of surgical guide structure according to the present invention.

A modified form of surgical guide structure, according to the present invention, is shown at 190 in FIG. 7. The guide structure 190 is similar to that 10 shown in FIGS. 1-5 and includes a guide tube 192, a surrounding, slotted, second tube 194, a ratchet mechanism at 196 operable by radially projecting arms 198, 200, a sealing member 202 with a conical sealing surface 204, and a mechanism 206 to facilitate maintaining of the guide structure 190 in its operative position.

An outer sleeve 208 loosely surrounds the second tube 194 and is maintained in coaxial relationship therewith by a tapered locating boss 210, which fits in an opening 212 at a proximal end 214 of the outer sleeve 208. The outer sleeve 208 is preferably clear to allow viewing of graduations 216 on the second tube 194 to give an indication of the amount of penetration of the distal end 218 of the second tube 194 within the cavity within which the operation is being performed.

A single coil spring 220 surrounds the second tube 194 and resides partially within a radial space 222 between the second tube 194 and outer sleeve 208. The spring 220 exerts a bias between a housing 224 on the ratchet mechanism 196 and the sealing member 202.

The mechanism 206 has an arm 226 projecting radially outwardly of the structure 190 to support a tenaculum (not shown). The mechanism 206 has an integral sleeve 228 which guides axial movement relative to the underlying sleeve 208. A set screw 230 holds the sleeve 228 in a desired position relative to the outer sleeve 208. By tightening the set screw 230, the sleeve 208 is slightly collapsed in a radial direction so that the relative positions of the outer sleeve 208 and sleeve 228 are positively maintained.

It should be understood that while the inventive structure is particularly useful as an intrauterine guide, it is useful in any environment wherein an instrument is passed through a tissue to perform a surgical procedure within a cavity bounded by the tissue.

The inventive structure is also functional as a self-contained instrument in repositioning organs and vessels, according to another aspect of the invention, to facilitate the performance of surgical procedures. While the inventive method can be practiced to reposition various different organs and vessels, it is particularly useful in repositioning the uterus 12 upon introduction through the vagina 34. It should be understood that this particular procedure is only exemplary, as the same principal is employed in repositioning other organs and vessels.

The inventive method is described below with respect to FIGS. 6, 8 and 9, with the exemplary guide structure 164 serving as a self-contained repositioning instrument. All of the features described with respect to the guide structures 50, 190, are contemplated to be incorporated into the instrument 164, i.e. the operating arms 198, 200, the ratchet mechanism 196, the graduations 216, etc. The guide structure/instrument 164 is initially directed through the vagina 34 to place an elongate section 302 at the distal end of the instrument 164 within the uterus 12.

Figure 8:
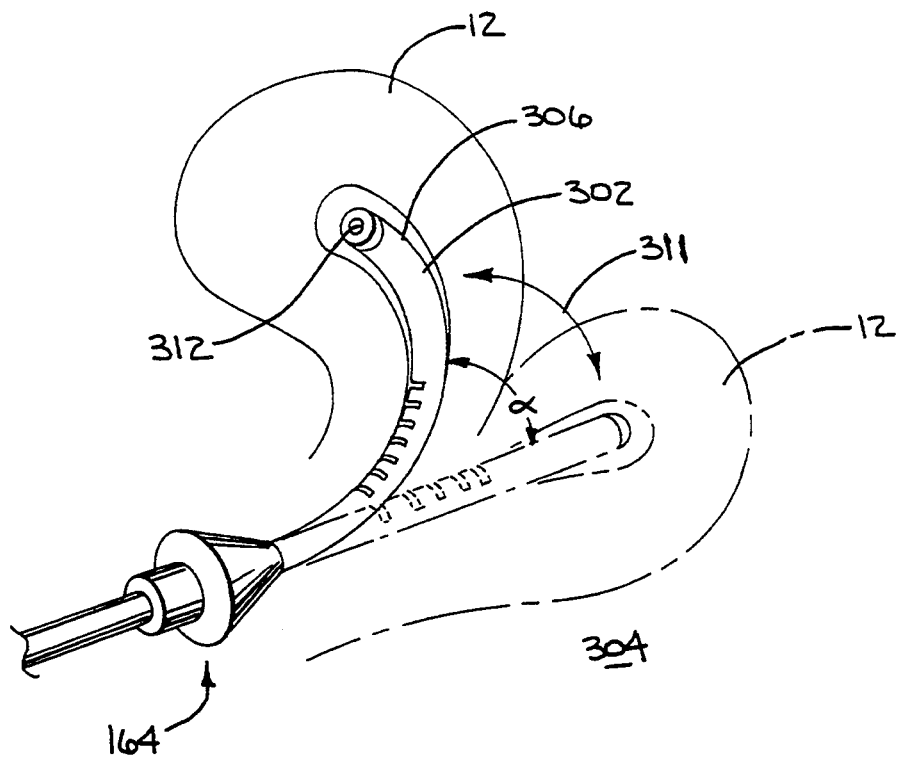
FIG. 8 is a schematic perspective view of the inventive instrument shown repositioning a uterus from a retroverted position to an anterior position.
Figure 9:
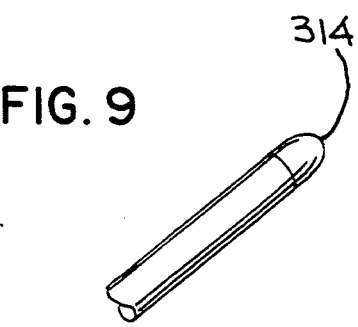
FIG. 9 is a perspective view of a modified form of distal end on the inventive instrument.

The uterus 12 in FIG. 8 is shown in a retroverted position, which is a condition common to women who have borne children. In this position, the uterus 12 sags downwardly into the peritoneal cavity 304. To properly access the uterus 12 through the vagina 34, it is necessary to place the uterus 12 in the anterior position shown in solid lines in FIG. 8. This is accomplished by rotating the instrument 164 approximately 90° about its axis, from the position previously described, so that reconfiguration/bending of the elongate section 302 of the instrument 164 causes the outer surface 306 of the elongate section 302 to bear upwardly on the uterus 12 to effect repositioning thereof.

The instrument 164 can be connected to the patient or, alternatively, it can be attached to a fixed support 308 through an appropriate means 310, as may allow the instrument 164 to be reoriented and fixed in any desired position. The support 308 could be, for example, a table supporting the patient or another fixed structure, such as a wall or ceiling within the operating room, a solid support upon the floor, etc. With this arrangement, the instrument 164 can be consistently maintained in a desired position within the uterus 12, whereupon reconfiguration of the elongate section 302 can be carried out to reposition the uterus 12.

According to the inventive method, the instrument 164 can be readily inserted into the uterus 12, without requiting an accessing incision. With the instrument 164 on the support 308, the surgeon can positively maintain the position of the instrument 164 without applying a constant pressure on the instrument 164 or relying on the patient as a support therefor. The elongate section 302 can then be readily reconfigured in the plane indicated by the double-headed arrow 312 through a prescribed angular range, identified by the angle α.

The surgeon is afforded a visual indication of the location of the repositioned uterus through the external indicia/graduations 216, taking the guess work common to conventional techniques, out of the procedure. The elongate section 302 is very compact, yet can be constructed to be positively reconfigured during a procedure. The ratchet mechanism 196 allows the surgeon to precisely, incrementally reposition the uterus 12 and maintain a desired position thereof.

All of the guide structures 50, 164, 190 are equally capable of performing the above two functions. That is, in addition to the guide function performed by the guide tube 192, the organ/vessel repositioning function is inherent in the operation of each guide structure 50, 164, 190.

In the event that there is no need for the internal passageway 312 defined by the guide tube 192, a rounded, bullet-shaped end piece 314 can be placed at the free end of the elongate section 302. This end piece 314, while blocking the passageway 312, guides the elongate section 302 readily past obstructions as the instrument 164 is inserted.

The foregoing disclosure of specific embodiments is intended to be illustrative of the broad concepts comprehended by the invention.

I claim:

1. A method of repositioning a uterus, said method comprising the steps of:

providing an instrument having a first bendable tube having an elongate section with an exposed surface, a second tube that is slidable within the first tube, means cooperating between the first and second tubes for reconfiguring the elongate section on the first tube from a first substantially straight state to a second bent state as an incident of only part of the first tube being moved lengthwise relative to the second tube, and means for maintaining the elongate section in a desired bent configuration:

directing the exposed surface on the elongate section through a patient's vagina and into the patient's uterus with the elongate section in the first state;

reconfiguring the elongate section to the second state by moving the part of the first tube relative to the second tube to thereby cause the exposed surface of the elongate section to bear against the patient's uterus to thereby reposition the uterus; and fixing the elongate section in its second state to thereby maintain the uterus in a desired position.

2. The method of repositioning a uterus according to claim 1 wherein the reconfiguring step comprises the step of bending the elongate section to move the uterus from a retroverted position to an anterior position.

3. The method of repositioning a uterus according to claim 1 including the step of attaching the instrument to the patient's cervix before reconfiguring the elongate section.

4. The method of repositioning a uterus according to claim 1 including the step of providing a tenaculum and attaching the tenaculum to the patient's cervix and the instrument to maintain the instrument in a desired position relative to the patient's cervix.

5. The method of repositioning a uterus according to claim 1 wherein the instrument includes a ratchet means for maintaining the elongate section in a plurality of predetermined states between said first and second states and reconfiguring the elongate section in increments between the first and second states.

6. The method of repositioning a uterus according to claim 1 including the steps of providing first and second arms on the instrument that are movable towards and away from each other and means responsive to movement of the first and second arms towards and away from each other for reconfiguring the elongate section between its first and second states and moving the first and second arms towards and away from each other to reconfigure the elongate section.

7. The method of repositioning a uterus according to claim 6 wherein the first and second arms are translatable relative to each other and including the steps of holding one of the arms in the palm of one of the user's hand and grasping the other of the arms with a plurality of fingers and drawing the plurality of fingers towards the palm of the user's hand to thereby reconfigure the elongate section.

8. The method of repositioning a uterus according to claim 7 wherein at least one of the first and second arms is translatable relative to the other of the first and second arms and including the step of gripping the first and second arms and squeezing the first and second arms together to translate the one of the first and second arms relative to the other of the first and second arms to thereby reconfigure the elongate section.

9. The method of repositioning a uterus according to claim 1 including the step of attaching the instrument to a rigid support so that the instrument can be consistently maintained in desired position relative to a in patient.

* * * * *